(12) United States Patent
Tezuka et al.

(10) Patent No.: US 11,503,981 B2
(45) Date of Patent: Nov. 22, 2022

(54) FLEXIBLE TUBE INSERTION APPARATUS AND FLEXIBLE TUBE INSERTION METHOD

(71) Applicant: OLYMPUS CORPORATION, Tokyo (JP)

(72) Inventors: Ryo Tezuka, Hachioji (JP); Hirokazu Nishimura, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 471 days.

(21) Appl. No.: 16/507,509

(22) Filed: Jul. 10, 2019

(65) Prior Publication Data

US 2019/0328211 A1    Oct. 31, 2019

Related U.S. Application Data

(63) Continuation of application No. PCT/JP2017/001011, filed on Jan. 13, 2017.

(51) Int. Cl.
*A61B 1/00* (2006.01)
*A61B 1/005* (2006.01)
*A61B 34/20* (2016.01)

(52) U.S. Cl.
CPC ...... *A61B 1/00055* (2013.01); *A61B 1/00009* (2013.01); *A61B 1/00045* (2013.01); *A61B 1/0057* (2013.01); *A61B 34/20* (2016.02)

(58) Field of Classification Search
None
See application file for complete search history.

(56) References Cited

U.S. PATENT DOCUMENTS 5,060,632 A * 10/1991 Hibino ............... A61B 1/0052
                                                    600/109
6,563,107 B2 * 5/2003 Danisch ................ D07B 1/145
                                                    250/227.16

(Continued)

FOREIGN PATENT DOCUMENTS

JP     2000-342520 A   12/2000
JP        4274854 B2    6/2009
WO   WO 2007/023631 A1  3/2007

OTHER PUBLICATIONS

English translation of International Preliminary Report on Patentability dated Jul. 25, 2019, together with the Written Opinion received in related International Application No. PCT/JP2017/001011.

(Continued)

*Primary Examiner* — Michael J Carey
*Assistant Examiner* — Minqiao Huang
(74) *Attorney, Agent, or Firm* — Scully, Scott, Murphy & Presser, P.C.

(57) ABSTRACT

A flexible tube insertion apparatus includes a flexible tube having flexibility and configured to be inserted into an object to be inserted, one or more external force detectors disposed on the flexible tube and configured to detect a force of an external force applied to the flexible tube when the flexible tube is twisted in at least one direction, and a providing device configured to provide twisting information regarding a twisting direction of the flexible tube for releasing a loop section formed in the flexible tube, according to a direction in which the flexible tube is twisted and the detected force of the external force.

10 Claims, 13 Drawing Sheets

(56) References Cited

U.S. PATENT DOCUMENTS

| | | | | |
|---|---|---|---|---|
| 2007/0059989 A1* | 3/2007 | Kura | ................. | A61B 1/04 |
| | | | | 439/685 |
| 2009/0287055 A1* | 11/2009 | Okamoto | ............. | A61B 1/0052 |
| | | | | 600/152 |
| 2011/0208000 A1* | 8/2011 | Honda | ............... | A61B 1/00154 |
| | | | | 600/118 |
| 2012/0071752 A1* | 3/2012 | Sewell | ................ | A61B 34/74 |
| | | | | 600/424 |
| 2013/0267775 A1* | 10/2013 | Okamoto | ............. | A61B 1/0052 |
| | | | | 600/109 |
| 2014/0309625 A1* | 10/2014 | Okamoto | ............... | A61B 34/71 |
| | | | | 606/1 |
| 2015/0099926 A1* | 4/2015 | Davidson | ............... | A61B 34/20 |
| | | | | 600/103 |
| 2015/0230697 A1* | 8/2015 | Phee | ................. | A61B 1/05 |
| | | | | 600/106 |
| 2018/0177556 A1* | 6/2018 | Noonan | ............. | A61B 1/00149 |

OTHER PUBLICATIONS

International Search Report dated Mar. 28, 2017 issued in PCT/JP2017/001011.
English Abstract of corresponding JP 2004-358095 A, dated Dec. 24, 2004.

\* cited by examiner

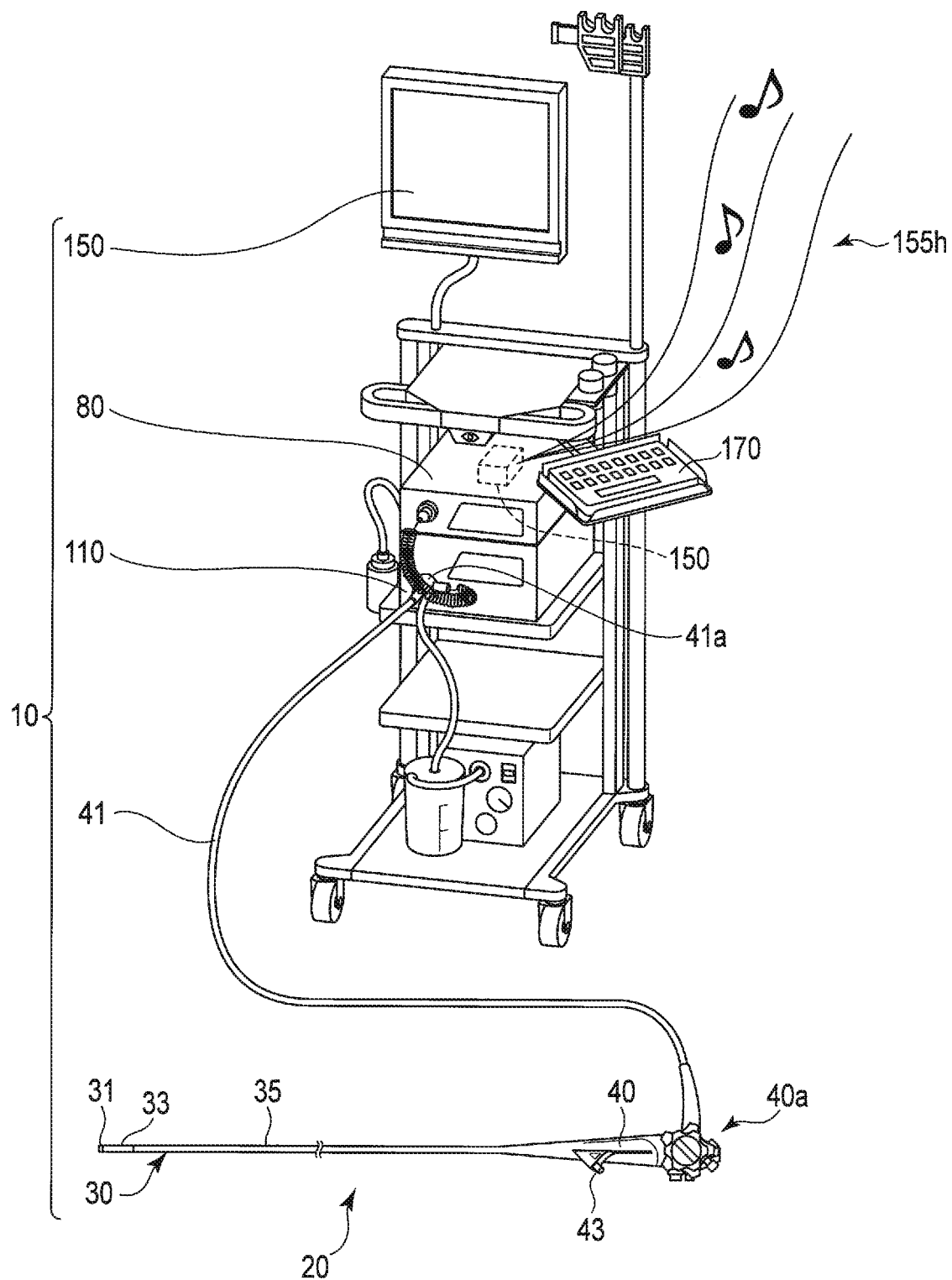
F I G. 1

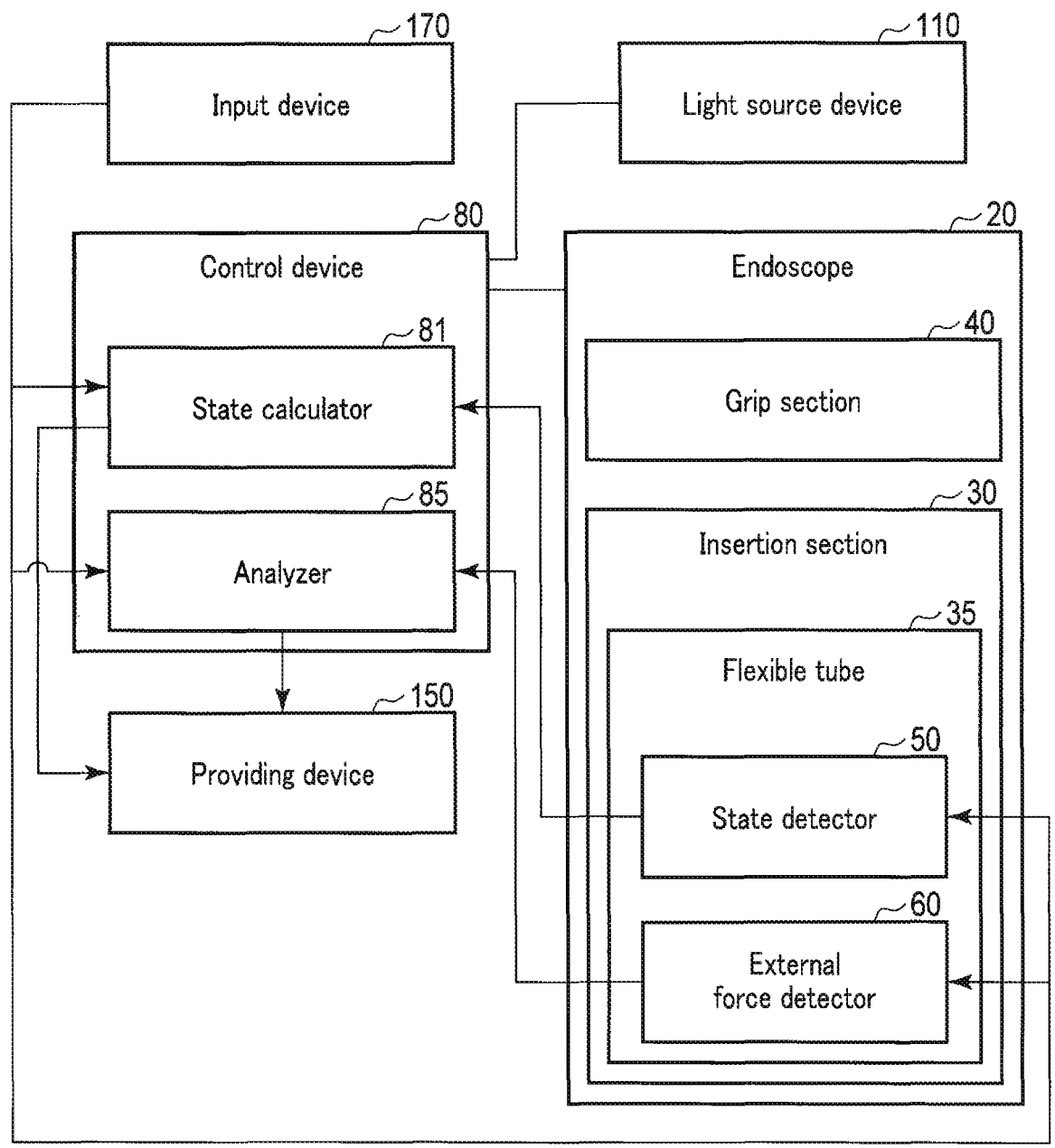
F I G. 2

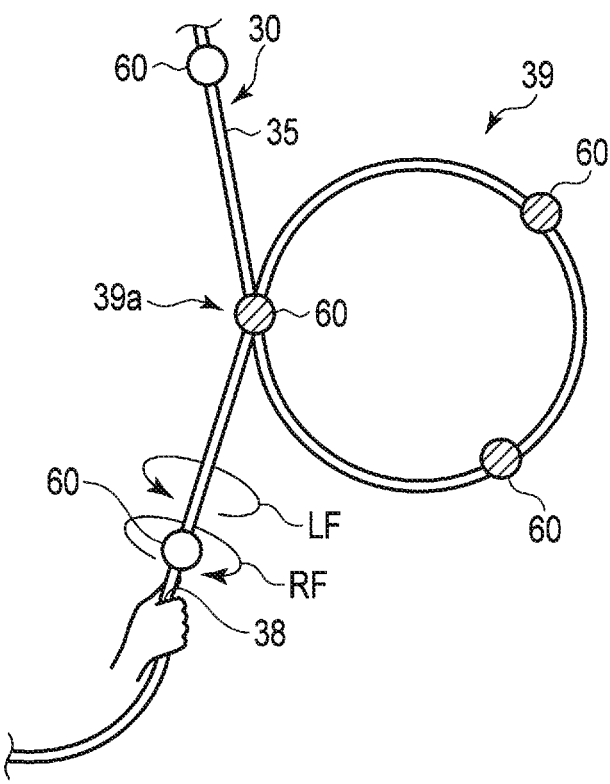
F I G. 3E
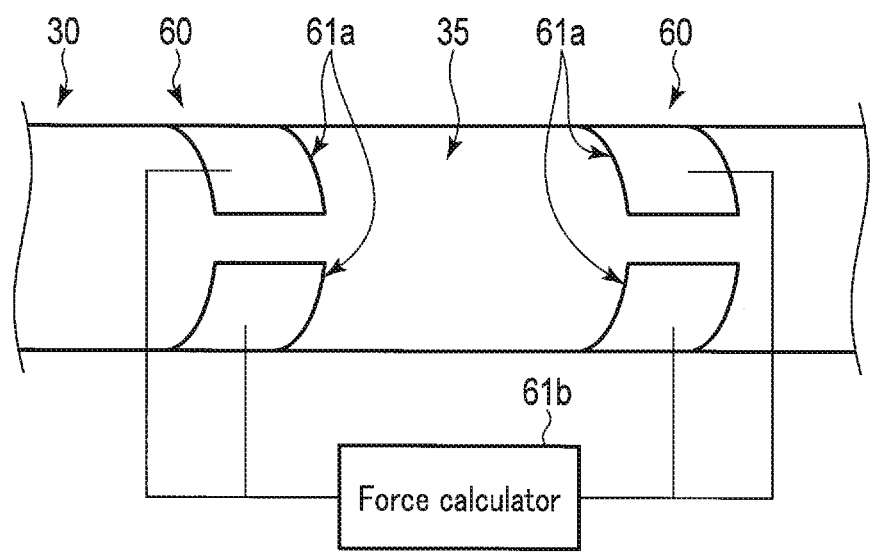
F I G. 4A

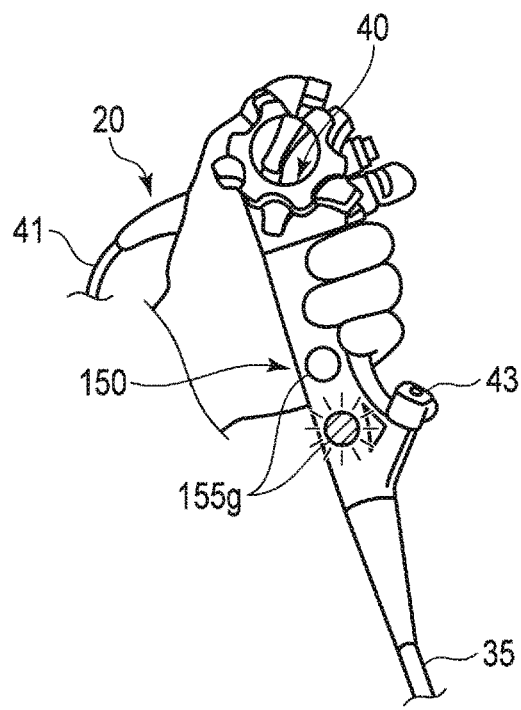
F I G. 5E
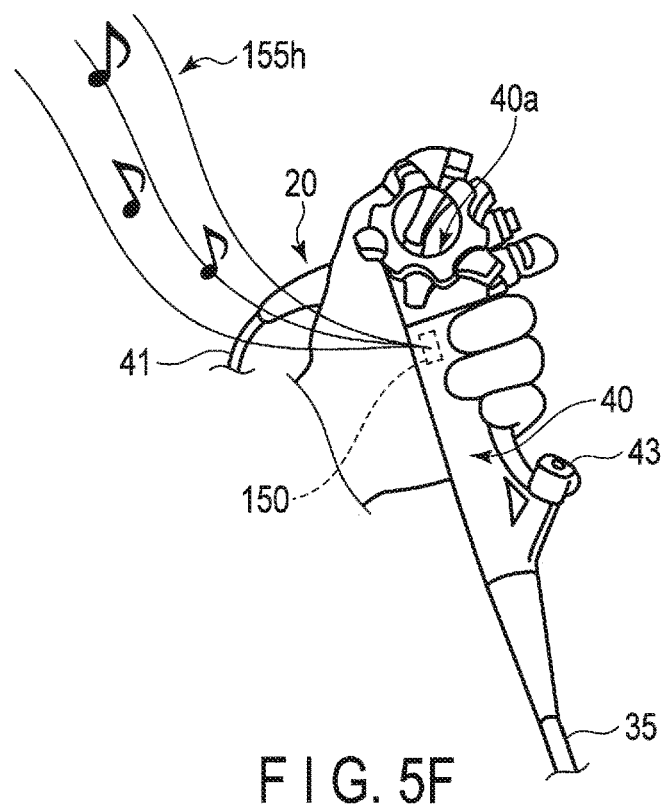
F I G. 5F

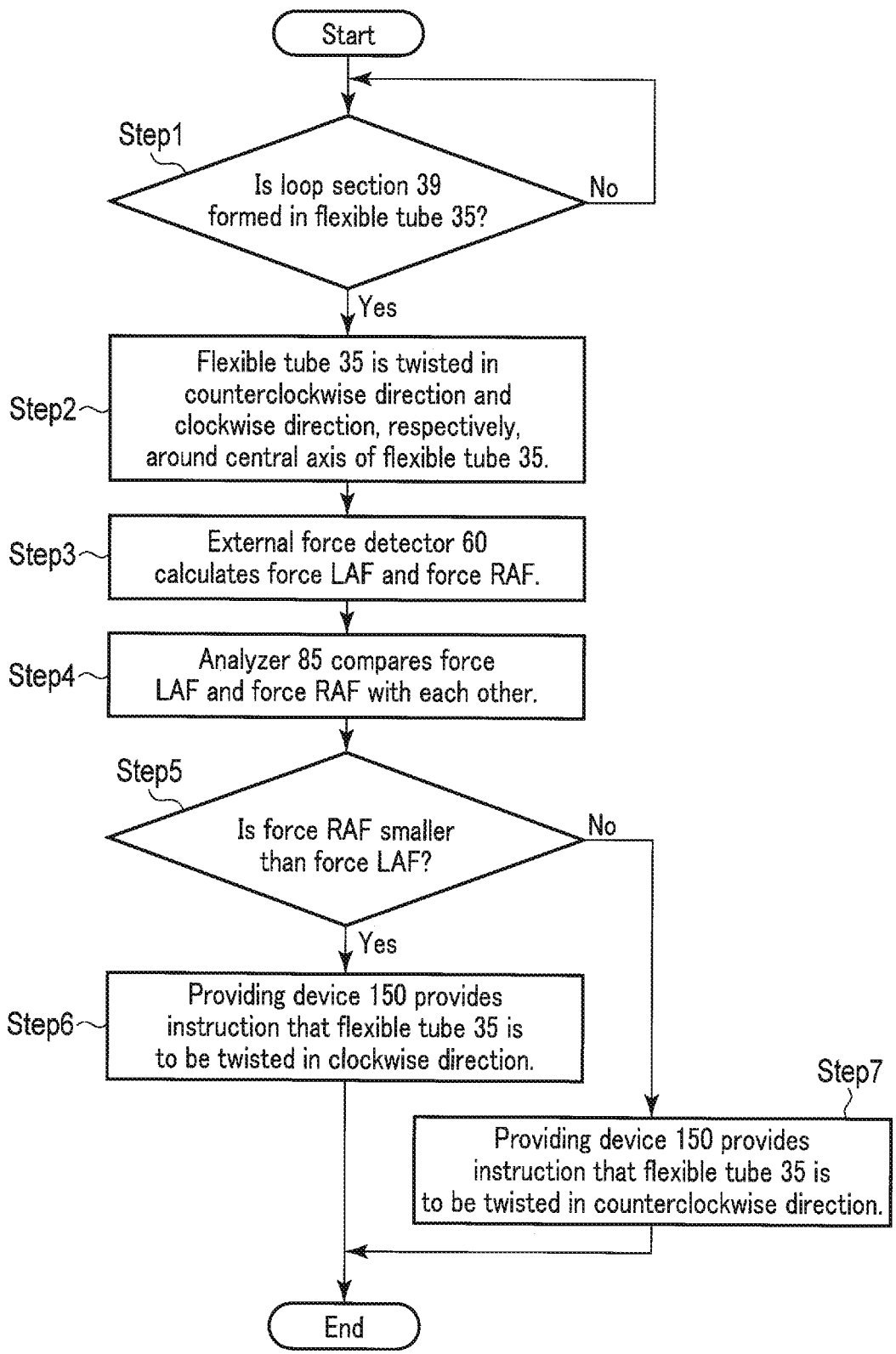
F I G. 6

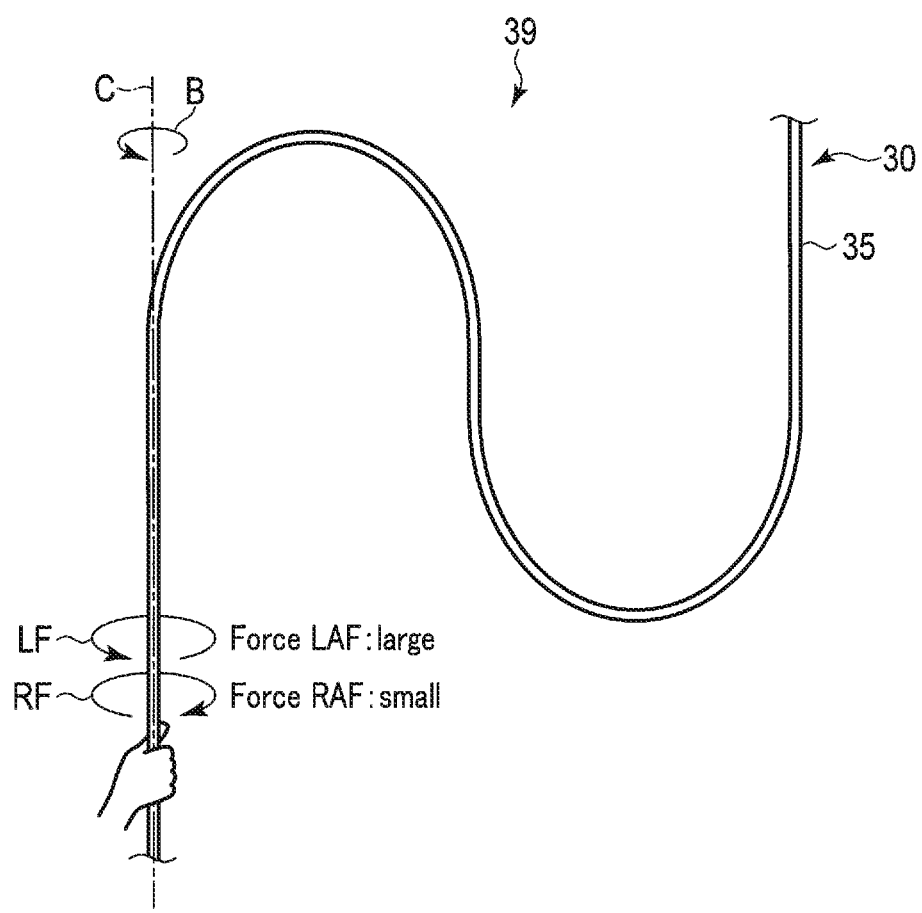
F I G. 7E

FLEXIBLE TUBE INSERTION APPARATUS AND FLEXIBLE TUBE INSERTION METHOD

CROSS-REFERENCE TO RELATED APPLICATIONS

This application is a Continuation Application of PCT Application No. PCT/JP2017/001011, filed Jan. 13, 2017, the entire contents of which are incorporated herein by reference.

BACKGROUND OF THE INVENTION

1. Field of the Invention

The present invention relates to a flexible tube insertion apparatus configured to insert a flexible tube toward a deep part of a pipeline section of an object to be inserted and a flexible tube insertion method.

2. Description of the Related Art

In insertion of a flexible tube of an endoscope into a large intestine, especially a sigmoid colon, a loop section may be formed in the flexible tube. If the loop section is formed in the sigmoid colon, the difficulty of insertion (progression) into the deep part such as a descending colon may be increased, and in addition, the large intestine is stretched by the loop section, which may cause pain to a patient due to stretching. Therefore, it is needed that the formed loop section is eliminated, and the flexible tube is changed to a substantially linear state. Therefore, in general, the loop section is eliminated by performing a twisting (rotation) operation of the insertion technique for the flexible tube, and the flexible tube is changed to the substantially linear state.

A running state of the flexible tube in the large intestine and a length of the large intestine are different by each patient. In addition, the insertion technique also differs by each operator who operates the flexible tube. The shape and size of the formed loop section differ depending on these differences and the hardness and thickness of the flexible tube. When the operator performs the twisting operation on a hand side of the flexible tube with the one hand while the operator grips the hand side of the flexible tube with one hand, the difference in the shape and size of the loop section changes tactile information, which is transmitted from the hand side of the flexible tube to the one hand, and which is a different sense of resistance for each operator. Specifically, an operator skilled in a twisting operation (hereinafter, referred to as an expert) can obtain the tactile information accurately and finely, but an operator with less experience in a twisting operation (hereinafter, referred to as an inexperienced person) may obtain the tactile information inaccurately and ambiguously. The expert determines a twisting direction of the flexible tube in the twisting operation based on the sensed resistance. Meanwhile, for the inexperienced person, it is not easy to sense the resistance itself, to sense a difference in resistance, and to determine the twisting direction based on the resistance.

Thus, the difficulty of the insertion technique used for a large intestine endoscope examination is high, and the insertion technique is required to be skilled. Therefore, it is desirable to provide support information for insertion, such as an insertion method and an insertion operation instruction, when the insertion technique is performed.

Therefore, for example, Japanese Patent No. 4274854 discloses an endoscope insertion shape analyzing apparatus configured to calculate a position of a flexible tube inserted into a body cavity using a magnetic coil or the like and analyze a loop section based on the calculated position. The endoscope insertion shape analyzing apparatus provides a linearization operation method that eliminates the loop section based on the analysis result and changes the flexible tube into a substantially linear state as support information. A display of the endoscope insertion shape analyzing apparatus provides (displays) the twisting direction of the flexible tube to eliminate the loop section as the linearization operation method.

BRIEF SUMMARY OF THE INVENTION

A flexible tube insertion apparatus includes a flexible tube having flexibility and configured to be inserted into an object to be inserted, one or more external force detectors disposed on the flexible tube and configured to detect a force of an external force applied to the flexible tube when the flexible tube is twisted in at least one direction, and a providing device configured to provide twisting information regarding a twisting direction of the flexible tube for releasing a loop section formed in the flexible tube, according to a direction in which the flexible tube is twisted and the detected force of the external force.

A flexible tube insertion method includes detecting a force of an external force applied to a flexible tube having flexibility and configured to be inserted into an object to be inserted when the flexible tube is twisted in at least one direction, and providing twisting information regarding a twisting direction of the flexible tube for releasing a loop section formed in the flexible tube, according to a direction in which the flexible tube is twisted and the detected force of the external force.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a schematic view of a flexible tube insertion apparatus according to an embodiment of the present invention.

FIG. 2 is a diagram for explaining a relationship among a state detector, a state calculator, an external force detector, an analyzer, a providing device, and an input device.

FIG. 3E is a diagram showing an example of an arrangement position of external force detectors.

FIG. 4A is a diagram showing an example of a constitution of an external force detector.

FIG. 5E is a diagram showing an example of providing twisting information.

FIG. 5F is a diagram showing an example of providing twisting information.

FIG. 6 is a flowchart showing an operation method of a flexible tube insertion apparatus.

FIG. 7E is a diagram for explaining a calculation, a comparison, and a determination of the forces LAF and RAF according to a shape and a state of the loop section.

DETAILED DESCRIPTION OF THE INVENTION

Figure 3A:
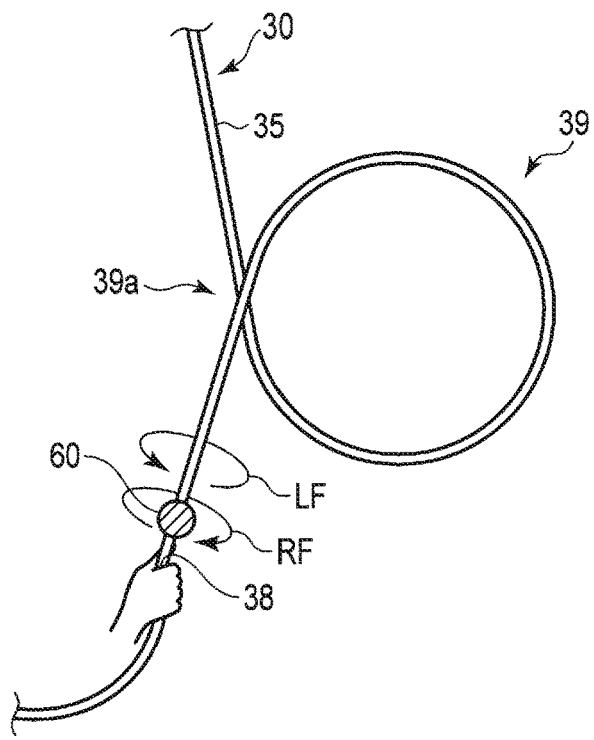
FIG. 3A is a diagram showing an example of an arrangement position of an external force detector.

Hereinafter, an embodiment of the present invention will be described with reference to the drawings. Further, in some drawings, the illustration of some of the members is omitted for clarity of illustration.

As shown in FIG. 1, a flexible tube insertion apparatus (hereinafter, referred to as an insertion apparatus 10) has an endoscope 20, a control device 80, a light source device 110, a providing device 150, and an input device 170. The control device 80 is connected to the endoscope 20, the light source device 110, the input device 170, and the providing device 150, and the control device 80 controls them. The control device 80 functions as the control device 80 configured to control support information for assisting insertion of a flexible tube 35 of the insertion section 30 disposed in the endoscope 20, for example.

The light source device 110 emits illumination light for observation and imaging by the endoscope 20.

The control device 80 may function as a video processor having an image processing circuit (not shown) electrically connected to an imaging unit (not shown). The imaging unit is embedded in a distal end section of the insertion section 30, and has, for example, a CCD or the like. The imaging unit converts an optical image obtained from reflected light generated by reflecting the illumination light emitted from the distal end section of the insertion section 30 on an object to be observed into an electrical signal. The imaging unit outputs the electrical signal to the image processing circuit. The image processing circuit generates an image signal of the object to be observed based on the electrical signal.

The providing device 150 provides twisting information to be described later in the present embodiment. An example of the provision will be described later. The providing device 150 may provide an image 151 (e.g., see FIG. 5A) of the object to be observed based on the image signal generated by the image processing circuit. In this case, the providing device 150 has, for example, a monitor displaying the image 151.

The input device 170 is, for example, a general input device such as a keyboard. The input device 170 may be, for example, a pointing device such as a mouse, a tag reader, a button switch, a slider, a dial, or a foot switch. The input device 170 may be used by an operator to input various commands for operating the insertion apparatus 10. The input device 170 as the button switch may be embedded in a grip section 40 of the endoscope 20.

The endoscope 20 is, for example, a medical soft endoscope. The endoscope 20 may be, for example, an industrial soft endoscope, a catheter, or a treatment instrument. The endoscope 20 may have a soft insertion section 30 configured to be inserted into a pipeline section (e.g., an intestinal tract of a large intestine) of an object to be inserted (e.g., a patient). The insertion section 30 may have a flexible portion (e.g., a flexible tube 35) capable of being bent by an external force. The endoscope 20 may be a front-viewing endoscope or a side-viewing endoscope. The object to be inserted is not limited to, for example, human, but may be animals or other structures. The pipeline section may be, for example, an industrial pipe.

The endoscope 20 has the insertion section 30, the grip section 40 connected to a proximal end section of the insertion section 30 and configured to be gripped by the operator of the endoscope 20, and a universal cord 41 extending from a side surface of the grip section 40. The universal cord 41 has a connection section 41a detachably attached to the light source device 110. Since the light source device 110 is electrically connected to the control device 80, the endoscope 20 is electrically connected to the control device 80 through the light source device 110.

The insertion section 30 is tubular, elongated, and flexible. The insertion section 30 advances and retreats within the pipeline section with respect to the pipeline section. The insertion section 30 is an insertion body inserted into the pipeline section. The insertion section 30 has a distal end hard section 31 and a flexible tube 35 in this order from the distal end section of the insertion section 30 to a proximal end section of the insertion section 30. The distal end hard section 31 is shorter than the flexible tube 35. Therefore, in the present embodiment, the distal end hard section 31 and a distal end section of the flexible tube 35 are regarded as the distal end section of the insertion section 30. In addition, the distal end section of the flexible tube 35 has a bendable section 33, the bendable section 33 is regarded as the distal end section of the flexible tube 35, and the bendable section 33 is included in the flexible tube 35. That is, the flexible tube 35 has the bendable section 33 that is actively bent by an operation of the grip section 40 and a flexible section excluding the bendable section 33. The flexible section is passively bent by an external force. The flexible tube 35 is bendable according to the shape of the pipeline section. The flexible tube 35 is flexible and is deflected by the external force. The bendable section 33 bends in a desired direction by a knob 40a arranged on the grip section 40.

As shown in FIG. 2, the insertion apparatus 10 has a state detector 50 configured to detect state information of the flexible tube 35 regarding a state of the flexible tube 35 including the bendable section 33. The state information includes a bending state of the flexible tube 35 including the bendable section 33. The bending state of the flexible tube 35 includes, for example, a bending quantity (magnitude of bending) of the flexible tube 35 including the bendable section 33. The bending quantity is, in other words, a curvature radius or a curvature. The bending state of the flexible tube 35 includes a bending direction of the flexible tube 35 including the bendable section 33.

The state detector 50 has a fiber sensor configured to utilize loss in light transmission quantity due to a bending of an optical fiber 51 (see FIG. 4C), as an example. The fiber sensor has a light source (not shown) configured to emit light, the optical fiber 51 configured to guide the light, and a reflector (not shown) configured to reflect the light in order for the light guided by the optical fiber 51 to reverse the optical fiber 51. The fiber sensor has a light receiver (not shown) configured to receive the light reflected by the reflector and a light branching unit (not shown). The state detector 50 is disposed in the endoscope 20 and the control device 80, but for the sake of clarity of illustration, in FIG. 2, the state detector 50 is illustrated in the flexible tube 35, which is a portion where the optical fiber 51 is disposed. The light source has, for example, an LED or the like. The light source is a separate entity from the light source of the light source device 110 configured to emit light for observation and imaging. The optical fiber 51 is embedded in the endoscope 20 and has flexibility. The optical fiber 51 has sections to be detected (not shown) mounted on the insertion section 30. The sections to be detected are disposed at different positions in a longitudinal axis direction of the optical fiber 51. For example, the sections to be detected may be disposed on a portion for calculating shape information of the flexible tube 35, a portion for detecting an external force applied to the flexible tube 35, and the like to be described later. In the present embodiment, the sections to be detected are disposed to be spaced apart from each other at equidistant intervals. The reflector is disposed at a distal end section of the optical fiber 51 positioned at the distal end section of the insertion section 30. The light receiver may have, for example, a spectroscopic element such as a spectroscope or a color filter, and a light receiving element such as a photodiode. The light source, the light receiver, and a proximal end section of the optical fiber 51 are optically connected to the light branching unit. The light branching unit has, for example, an optical coupler or a half mirror. The light branching unit guides the light emitted from the light source to the optical fiber 51, and also guides returned light reflected by the reflector and guided by the optical fiber 51 to the light receiver. That is, the light travels in the order of the light source, the light branching unit, the optical fiber 51, the reflector, the optical fiber 51, the light branching unit, and the light receiver. The light source, the light receiver, and the light branching unit are mounted on the control device 80, for example.

When the insertion section 30 is bent, the optical fiber 51 is bent in accordance with the bending. Accordingly, a part of the light propagating through the optical fiber 51 exits (leaks) to the outside through, for example, the section to be detected having sensitivity to different wavelengths. The section to be detected changes optical characteristic of the optical fiber 51, for example, light transmission quantity of light of a predetermined wavelength. Therefore, when the optical fiber 51 is bent, the light transmission quantity of the light guided in the optical fiber 51 is changed according to bending quantity. The optical signal including information on the change in the light transmission quantity is received by the light receiver. The light receiver outputs the optical signal, as state information, to the state calculator 81, which will be described later, disposed in the control device 80.

In addition, one section to be detected may be disposed on one optical fiber 51, and in this case, optical fibers 51 are disposed. In addition, it is assumed that sections to be detected are disposed at the same position or near position in the longitudinal axis direction of the optical fiber 51 and at different positions in a direction around a central axis in the longitudinal axis direction of the optical fiber 51. In this case, it is possible to detect the bending quantity and the bending direction by a combination of the detection results of the sections to be detected.

The state detector 50 is not limited to having the fiber sensor. The state detector 50 may have, for example, any one of a strain sensor, an acceleration sensor, a gyro sensor, an element such as a coil, and a position sensor. The strain sensor detects, for example, a bending strain generated in the flexible tube 35 by an external force (pressure) that the flexible tube 35 receives from the outside of the flexible tube 35 (e.g., an inner peripheral wall section of the pipeline section). The acceleration sensor detects an acceleration of the flexible tube 35. The gyro sensor detects an angular velocity of the flexible tube 35. The element generates a magnetic field in response to a state of the flexible tube 35 such as the shape of the flexible tube 35.

The state detector 50 always detects (operates) after a detection start instruction is input from the input device 170 to the state detector 50. A timing of the detection may be performed every time a certain time elapses, and is not particularly limited. The state detector 50 is connected to the state calculator 81 by, for example, a wired manner or a wireless manner, and outputs the detection result detected by the state detector 50 to the state calculator 81.

As shown in FIG. 2, the insertion apparatus 10 has one or more external force detectors 60, the state calculator 81, and an analyzer 85. The external force detectors 60 are disposed on, for example, the flexible tube 35. The state calculator 81 and the analyzer 85 are disposed on the control device 80, for example.

The state calculator 81 and the analyzer 85 are constituted by a hardware circuit including an ASIC and the like. At least one of the state calculator 81 and the analyzer 85 may be constituted by a processor. When at least one of the state calculator 81 and the analyzer 85 is constituted by the processor, an internal memory (not shown) or an external memory (not shown) to which the processor can access is disposed. The internal memory or external memory stores a program code executed by the processor to cause the processor to function as at least one of the internal memory and the external memory.

The analyzer 85 may be disposed on the grip section 40 as long as it is constituted by a hardware circuit.

The state calculator 81 calculates shape information of the flexible tube 35 including the bendable section 33 regarding the shape of the flexible tube 35 including the bendable section 33 along the central axis direction of the flexible tube 35, based on the state information detected by the state detector 50. Specifically, the state calculator 81 calculates the shape information, specifically, a bent shape of the flexible tube 35 in an actually bent portion, based on the state information output from the state detector 50, for example. The bent shape includes, for example, the bending quantity and the bending direction of the flexible tube 35 including the bendable section 33. The shape information includes position information of the external force detector 60. For example, since the position information of the external force detector 60 in the flexible tube 35 is preset, a position of the external force detector 60 is overlapped with the calculated bent shape, so that the shape information includes the position information of the external force detector 60. In addition, the state calculator 81 may calculate the position information of the external force detector 60 based on an output of a sensor 61a of the external force detector 60 to be described later.

Figure 5A:
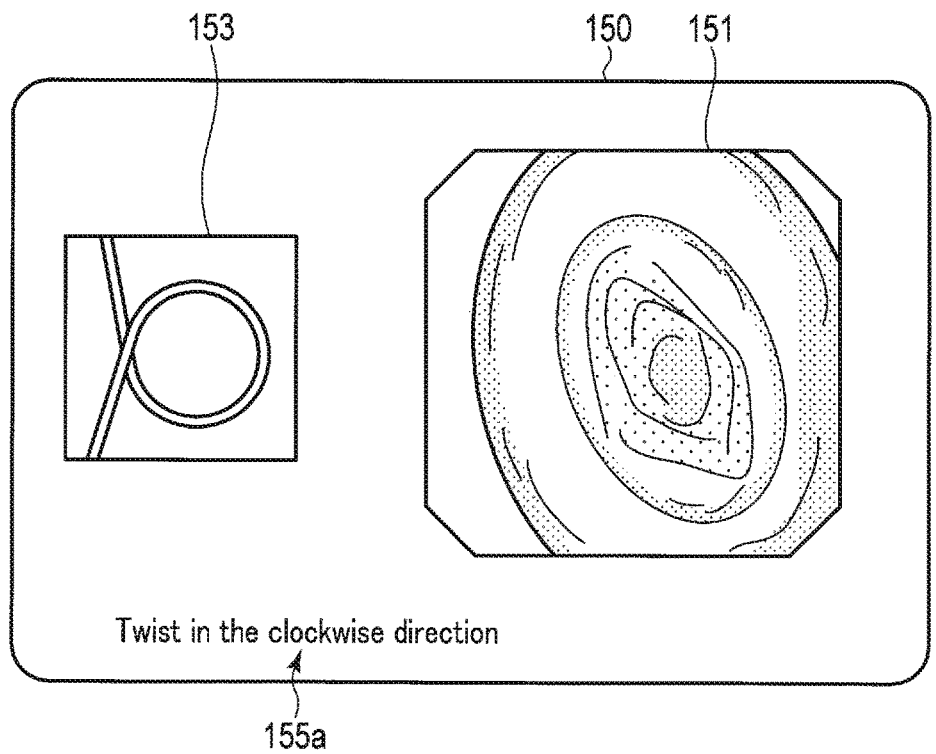
FIG. 5A is a diagram showing an example of providing twisting information.

The state calculator 81 may output the shape information calculated by the state calculator 81 to the providing device 150, and the providing device 150 may display the shape information as an image 153 (see FIG. 5A). The image 153 may indicate the position of the external force detector 60 in the shape information. The state calculator 81 always calculates (operates) after a calculation start instruction output from the input device 170 is input to the state calculator 81 in a state in which the detection result of the state detector 50 is input. In addition, a calculation timing may be performed every time a certain time elapses, and is not particularly limited.

The external force detector 60 is disposed on the flexible tube 35, detects an external force applied to the flexible tube 35, and calculates a value of the detected external force. As shown in FIGS. 3A, 3B, 3C, 3D, and 3E, for example, it is assumed that a hand side is twisted to a clockwise direction and a counterclockwise direction, respectively, around the central axis of the flexible tube 35 by one hand while the hand side of the flexible tube 35 is gripped by the one hand of the operator. In such a twisting operation, for example, a left twisting operation in the counterclockwise direction is performed, and a right twisting operation in the clockwise direction is performed after the left twisting operation. The right twisting operation continues with the left twisting operation. The order of the left twisting operation and the right twisting operation is not particularly limited. A time interval between the left twisting operation and the right twisting operation may be adjusted as desired. A twisting force of the operator given from the one hand to the hand side of the flexible tube 35 is transmitted from the hand side of the flexible tube 35 to the distal end section side of the flexible tube 35. As a result, the flexible tube 35 is twisted to the counterclockwise direction and the clockwise direction, respectively, around the central axis of the flexible tube 35. In this case, the external force detector 60 detects a twisting force in the counterclockwise direction (hereinafter, referred to as external force LF) and a twisting force in the clockwise direction (hereinafter, referred to as external force RF), respectively, as the external force. Here, the counterclockwise direction and the clockwise direction indicate the directions around the central axis of the flexible tube 35 when the distal end section side of the flexible tube 35 is viewed from the hand side of the flexible tube 35 in the central axis direction of the flexible tube 35. The external force detector 60 detects the external force LF in the counterclockwise direction and the external force RF in the clockwise direction, and calculates a force (hereinafter, referred to as a force LAF) of the external force LF and a force (hereinafter, referred to as a force RAF) of the external force RF. Specifically, the external force detector 60 calculates the force LAF based on the detected external force LF, and calculates the force RAF based on the detected external force RF. In other words, the external force detector 60 measures the forces LAF and RAF of the external forces LF and RF applied to the flexible tube 35 in the external force detector 60. Therefore, the forces LAF and RAF are the measured values measured by the external force detector 60, and are the values of the detected external forces LF and RF, which are quantitative information. In this way, the external force detector 60 calculates the forces LAF and RAF, which are the measured values. The external force detector 60 may detect not only the twisting force but also the other forces as the external force. The other forces indicate, for example, a reaction force received by the flexible tube 35 from the intestinal wall around the flexible tube 35 or from organs around the flexible tube 35.

The external force detector 60 outputs the forces LAF and RAF to the analyzer 85. The external force detector 60 always detects (operates) after a detection start instruction output from the input device 170 is input to the external force detector 60. In addition, a detection timing may be performed every time a certain time elapses, and is not particularly limited.

Here, Examples 1 to 3 of a constitution of the external force detector 60 will be described.

As shown in FIG. 4A, as Example 1, the external force detector 60 may have one or more sensors 61a. Like the state detector 50, the sensors 61a may have, for example, any one of a strain sensor, an acceleration sensor, a gyro sensor, an element such as a coil, a position sensor, and a fiber sensor. For example, the sensors 61a are disposed on a peripheral surface of the flexible tube 35. For example, the sensors 61a are disposed directly on an outer peripheral surface of the flexible tube 35. Sensors 61a may be disposed to be spaced apart from each other at equidistant intervals in the direction around the central axis of the flexible tube 35. In addition, when external force detectors 60 are disposed on the flexible tube 35, for example, the external force detectors 60 are disposed to be spaced apart from each other at equidistant intervals in the direction of the central axis of the flexible tube 35, and the sensors 61a on each external force detector 60 may be disposed to be spaced apart from each other at equidistant intervals in the direction of the central axis of the flexible tube 35. Each of the sensors 61a detects the bending strain generated in the flexible tube 35 by the twisting when the flexible tube 35 is twisted to the counterclockwise direction and the clockwise direction around the central axis of the flexible tube 35 as the external forces LF and RF. The sensors 61a output the external forces LF and RF to a force calculator 61b. The force calculator 61b calculates the force LAF based on the external force LF and calculates the force RAF based on the external force RF. The force calculator 61b outputs the calculated forces LAF and RAF to the analyzer 85. The force calculator 61b may be included in the external force detector 60. Like the state calculator 81, the force calculator 61b may be constituted by, for example, a hardware circuit including an ASIC, and may be constituted by a processor. The force calculator 61b may be disposed on the control device 80 and may be disposed on the grip section 40. Although not shown in the present example, the external force detector 60 may also serve as the state detector 50 having the sensors 61a and the state calculator 81. In this case, the external force detector 60 detects the state information from the outputs of the sensors 61a as the state detector 50, and detects the external forces LF and RF. In addition, the external force detector 60 calculates the shape information as the state calculator 81, and calculates the forces LAF and RAF.

Figure 4B:
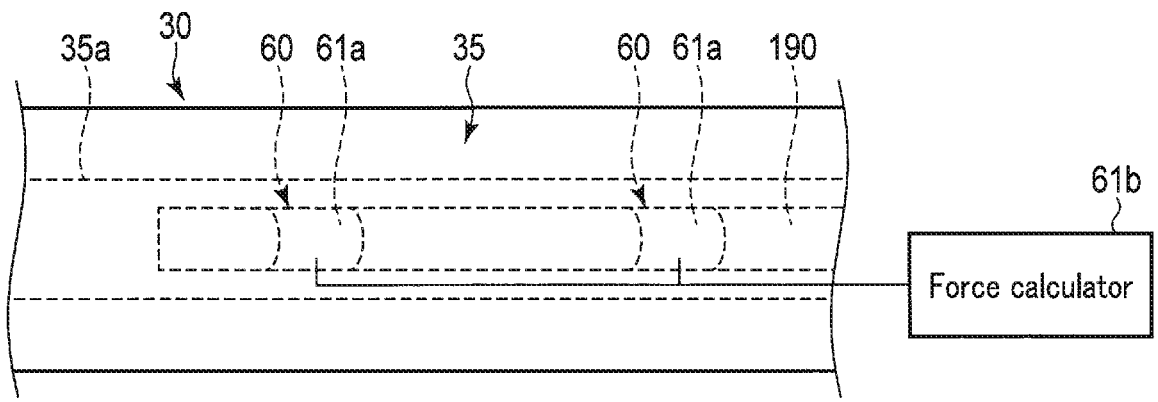
FIG. 4B is a diagram showing an example of a constitution of an external force detector.

As shown in FIG. 4B, as Example 2, the insertion apparatus 10 has a probe 190, and one or more sensors 61a may be disposed on a peripheral surface of the probe 190. Therefore, in the present example, the external force detector 60 has one or more sensors 61a disposed on the peripheral surface of the probe 190. For example, the sensors 61a are disposed directly on an outer peripheral surface of the probe 190. When external force detectors 60 are disposed on the probe 190, for example, the external force detectors 60 are disposed to be spaced apart from each other at equidistant intervals in the direction of the central axis of the probe 190, and the strain sensors on each external force detector 60 may be disposed to be spaced apart from each other at equidistant intervals in the direction of the central axis of the probe 190. Although not shown, sensors 61a may be disposed to be spaced apart from each other at equidistant intervals, for example, in the direction around the central axis of the probe 190.

The probe 190 is a separate entity from the flexible tube 35. The probe 190 has flexibility and is inserted into a channel 35a disposed inside the flexible tube 35 from an insertion port section 43 (see FIG. 1) disposed in the grip section 40. The outer peripheral surface of the probe 190 can abut an inner peripheral surface of the channel 35a. The abutting is performed, for example, when the flexible tube 35 is bent. The probe 190 can be inserted and extracted freely into and from the flexible tube 35. Such a probe 190 is considered to be an insert inserted into the pipeline section through the flexible tube 35. The probe 190 is positioned relatively to the flexible tube 35 in the direction of the central axis of the flexible tube 35 and the direction around the axis of the central axis thereof. Therefore, the sensors 61a disposed on the probe 190 are indirectly disposed on the flexible tube 35 through the probe 190. When the external force is applied to the flexible tube 35, the flexible tube 35 is bent. The probe 190 is bent in accordance with the bending of the flexible tube 35. As a result, the outer peripheral surface of the probe 190 abuts the inner peripheral surface of the channel 35a. When the external forces LF and RF are applied to the flexible tube 35, the flexible tube 35 is bent in accordance with the external forces LF and RF. For example, the external forces LF and RF are applied (transmitted) to the probe 190 through the abutting portion. The probe 190 is twisted according to the twisting of the flexible tube 35, in other words, according to the external forces LF and RF applied to the probe 190. The sensors 61a detect the external forces LF and RF applied to the probe 190 through the flexible tube 35 and detect the external forces LF and RF as the external forces LF and RF applied to the flexible tube 35.

Figure 4C:
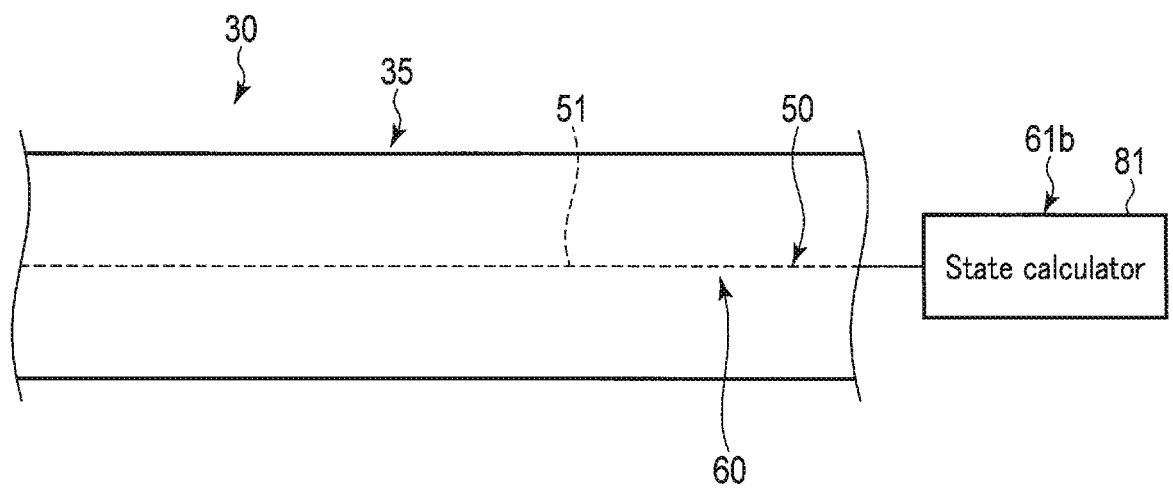
FIG. 4C is a diagram showing an example of a constitution of an external force detector.

As shown in FIG. 4C, as Example 3, the state detector 50 as the fiber sensors and the state calculator 81 may have a function of the external force detector 60. The state detector 50 detects the external forces LF and RF together with the state information. In addition, the state calculator 81 calculates the forces LAF and RAF together with the shape information. That is, the state calculator 81 functions as the force calculator 61b configured to calculate the forces LAF and RAF.

The analyzer 85 analyzes the force LAF of the external force LF in the counterclockwise direction and the force RAF of the external force RF in the clockwise direction, which are detected by the external force detector 60, when the flexible tube 35 is twisted to the counterclockwise direction and the clockwise direction, respectively, around the central axis of the flexible tube 35. In an example of the analysis, the analyzer 85 compares the force LAF of the external force LF in the counterclockwise direction with the force RAF of the external force RF in the clockwise direction. In addition, the analyzer 85 determines a small force of the compared two forces RAF and LAF. Specifically, the analyzer 85 determines whether or not the force RAF is smaller than the force LAF. That is, the analyzer 85 analyzes the two forces LAF and RAF to determine which of the two forces LAF and RAF is the small force. The analyzer 85 outputs the determination result to the providing device 150. The analyzer 85 always analyzes and determines after an analysis start instruction output from the input device 170 is input to the analyzer 85 in a state in which the calculation result of the external force detector 60 is input. In addition, timings of the analysis and determination may be performed every time a certain time elapses, and are not particularly limited.

Here, examples 1 to 5 of an arrangement position of the external force detector 60 and a comparison operation of the analyzer 85 corresponding to the respective examples 1 to 5 will be described with reference to FIGS. 3A, 3B, 3C, 3D, and 3E. For the comparison operation, it is assumed that the flexible tube 35 is twisted to the counterclockwise direction and the clockwise direction, respectively, around the central axis of the flexible tube 35. In such a twisting operation, for example, a left twisting operation in the counterclockwise direction is performed, and a right twisting operation in the clockwise direction is performed after the left twisting operation. The right twisting operation continues with the left twisting operation. The order of the left twisting operation and the right twisting operation is not particularly limited.

As shown in FIG. 3A, as Example 1, for example, an external force detector 60 is disposed on a gripped portion 38 of the flexible tube 35 to be gripped by the operator. The gripped portion 38 indicates an example of a position where an external force is applied to the flexible tube 35. The external force indicates, for example, a gripping force of the operator. The gripped portion 38 indicates, for example, a position spaced apart from a distal end section of the insertion section 30 by a desired length. The desired length indicates, for example, a length that a length of a rectum and a length of a sigmoid colon are added to each other, or a length longer than the above-mentioned length. The external force detector 60 calculates the forces LAF and RAF at the gripped portion 38. The analyzer 85 compares the force LAF and the force RAF with each other.

Figure 3B:
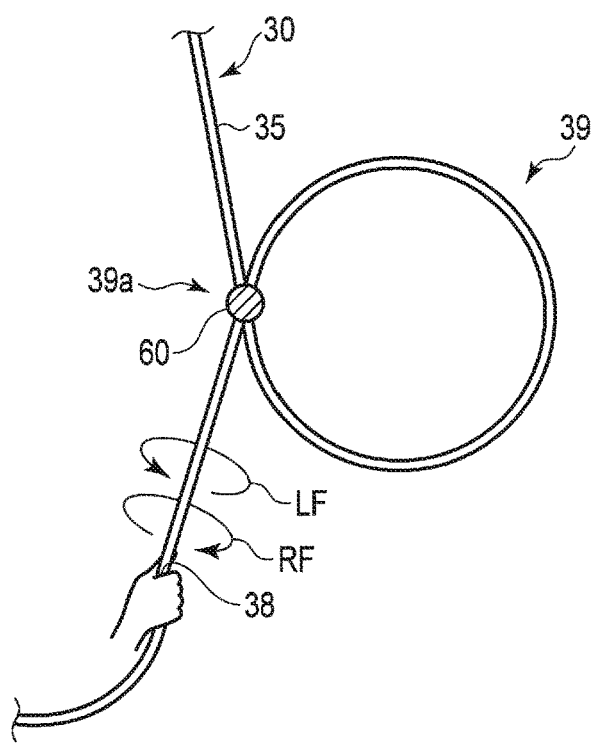
FIG. 3B is a diagram showing an example of an arrangement position of an external force detector.
Figure 3C:
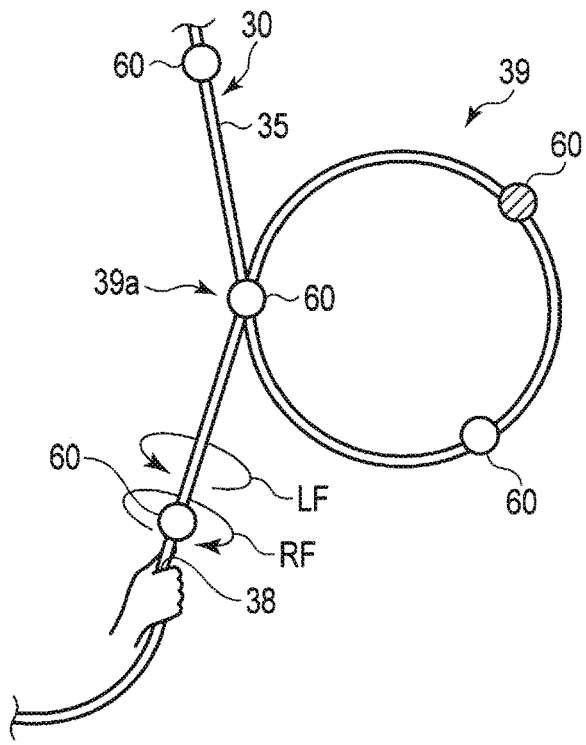
FIG. 3C is a diagram showing an example of an arrangement position of external force detectors.

As shown in FIG. 3B, as Example 2, for example, an external force detector 60 is disposed on the periphery of an intersecting portion 39a including the intersecting portion 39a of a loop section 39 formed in the flexible tube 35. The periphery of the intersecting portion 39a indicates an example of a position where a reaction force due to twisting occurs. In general, the intersecting portion 39a is often formed in the sigmoid colon. Therefore, the periphery of the intersecting portion 39a is, for example, the position spaced apart from the distal end section of the insertion section 30 by the length of the sigmoid colon. Although not shown in FIG. 3B, the external force detector 60 may be disposed on the distal end section side of the flexible tube 35 on the periphery of the intersecting portion 39a, or may be disposed on the proximal end section side of the flexible tube 35 placed on the distal end section side of the flexible tube 35. The external force detector 60 calculates forces LAF and RAF at the periphery of the intersecting portion 39a. The analyzer 85 compares the force LAF and the force RAF with each other. As shown in FIG. 3C, as Example 3, for example, external force detectors 60 are disposed to be spaced apart from each other at substantially equidistant intervals. For example, the external force detectors 60 are disposed within a range from the distal end section of the flexible tube 35 to the gripped portion 38. Each of the external force detectors 60 calculates forces LAF and RAF at each arrangement position. For example, the analyzer 85 analyzes the maximum force LAF from the forces LAF at the respective arrangements. In addition, the analyzer 85 compares the maximum force LAF with the force RAF at the arrangement position of the external force detector 60 that has calculated the maximum force LAF. In FIG. 3C, the external force detector 60 that the analyzer 85 uses for comparison is hatched with oblique lines and the external force detectors 60 that the analyzer 85 does not use for comparison are not hatched. In this way, the analyzer 85 analyzes the maximum force from the forces of the external forces in a first direction (counterclockwise direction or clockwise direction) around the central axis that are detected by each of the external force detectors 60. In addition, the analyzer 85 compares the maximum force with the force of the external force in a second direction (clockwise direction or counterclockwise direction), which is a direction opposite to the first direction, at the arrangement position of the external force detector 60 that has calculated the maximum force. The analyzer 85 compares the force LAF and the force RAF at one place with each other. The arrangement position of the external force detector 60 that has calculated the maximum force is the portion where a value of the reaction force, which is the main factor that the operator feels resistance, is the maximum. The reason for comparing the forces at the arrangement position is that when the flexible tube 35 is twisted to the counterclockwise direction and the clockwise direction, it is assumed that a difference between the force LAF in the counterclockwise direction and the force RAF in the clockwise direction at such an arrangement position is most significant.

Further, it is not necessary for the analyzer 85 to limit the analysis of the maximum force. For example, the analyzer 85 analyzes an N-th force (N is a natural number of one or more) from the maximum force, and may compare the N-th force with a force of the external force in the direction opposite to the first direction at the arrangement position of the external force detector 60 that has calculated the N-th force. N is set as desired by the input device 170, for example. The maximum value of N is the same as the number of the external force detectors 60. Examples 1 and 2 that use forces other than the maximum force for analysis and comparison will be briefly described. As Example 1, when the maximum value of the force is a value that is not related to the twisting (e.g., noise), the maximum value (e.g., an N-th value) that is not affected by noise is used for analysis and comparison. As Example 2, when the force LAF and force RAF that are compared at the arrangement position where the maximum force is calculated are the same as each other, the comparison and analysis are performed at the arrangement position where the next largest force is calculated.

Alternatively, for example, the analyzer 85 analyzes a portion where a change in the force is the maximum before and after the twisting from the forces in the first direction around the central axis that are detected by each of the external force detectors 60. In addition, the analyzer 85 may compare the force LAF of the external force LF in the counterclockwise direction and the force RAF of the external force RF in the clockwise direction at the portion where the change in the force is the maximum with each other.

Figure 3D:
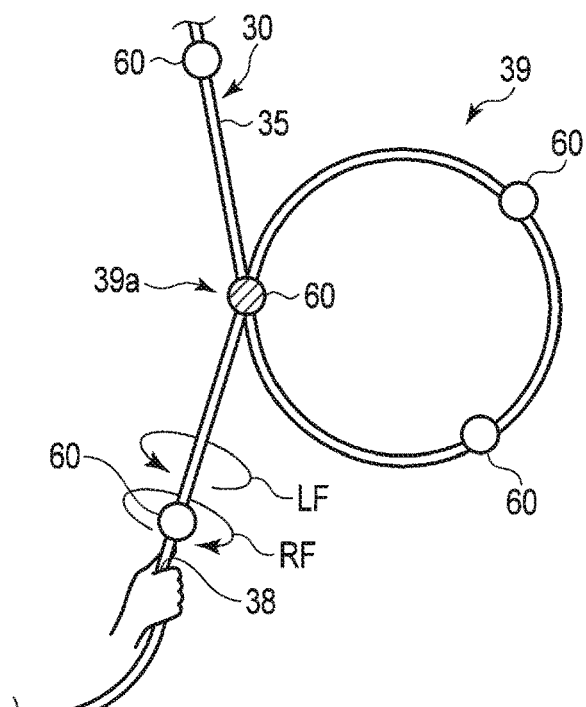
FIG. 3D is a diagram showing an example of an arrangement position of external force detectors.

As shown in FIG. 3D, as Example 4, for example, external force detectors 60 are disposed to be spaced apart from each other at substantially equidistant intervals. For example, the external force detectors 60 are disposed within a range from the distal end section of the flexible tube 35 to the gripped portion 38. Each of the external force detectors 60 calculates forces LAF and RAF at each arrangement position. For example, the analyzer 85 compares the force LAF of the external force LF and the force RAF of the external force RF with each other that are detected by the external force detector 60 disposed at the position where the reaction force due to the twisting occurs (e.g., the periphery of the intersecting portion 39a) from the detected forces LAF and RAF. In FIG. 3D, the external force detector 60 that the analyzer 85 uses for comparison is hatched with oblique lines and the external force detectors 60 that the analyzer 85 does not use for comparison are not hatched. The analyzer 85 compares the force LAF and the force RAF at one place with each other. In addition, the external force detector 60 disposed at the periphery of the intersecting portion 39a of the external force detectors 60 may be determined by the shape information. Therefore, the analyzer 85 may analyze the forces LAF and RAF detected by the determined external force detector 60.

As shown in FIG. 3E, as Example 5, for example, external force detectors 60 are disposed to be spaced apart from each other at substantially equidistant intervals. For example, the external force detectors 60 are disposed within a range from the distal end section of the flexible tube 35 to the gripped portion 38. Each of the external force detectors 60 calculates forces LAF and RAF at each arrangement position. For example, the analyzer 85 compares the total sum of the forces LAFs calculated by each of the external force detectors 60 disposed within a desired range and the total sum of the forces RAFs calculated by each of the external force detectors 60 disposed within the desired range with each other. In FIG. 3E, the external force detectors 60 that the analyzer 85 uses for comparison are hatched with oblique lines and the external force detectors 60 that the analyzer 85 does not use for comparison are not hatched. In this way, the analyzer 85 compares the total value of the forces LAFs at positions within the desired range with the total value of the forces RAFs at positions within the desired range. The desired range is set by the input device 170, for example. The desired range may be set as desired depending on the patient, the operator, and the like. The desired range indicates, for example, the loop section 39.

In the examples 3 to 5, the external force detectors 60 are disposed to be spaced apart from by substantially equidistant intervals, but the arrangement need not be limited thereto. The interval between the external force detectors 60 may be adjusted as desired. For example, in the distal end section of the flexible tube 35, the gripped portion 38, and a central portion between the distal end section of the flexible tube 35 and the gripped portion 38, the interval between the external force detectors 60 may be narrowed from the distal end section toward the central portion, and the interval between the external force detectors 60 may be narrowed from the gripped portion 38 to the central portion. That is, a large number of external force detectors 60 are disposed on the central portion side and a small number of external force detectors 60 are disposed on the distal end section side of the flexible tube 35 and the gripped portion 38 side.

The providing device 150 provides twisting information related to the twisting direction of the flexible tube 35 around the central axis of the flexible tube 35 in accordance with the analysis result of the analyzer 85. The providing device 150 provides the twisting direction corresponding to the small force determined by the analyzer 85 of the two compared forces LAF and RAF as the twisting information, based on the comparison result of the analyzer 85. The twisting information includes information instructing the twisting direction of the flexible tube 35 based on the comparison result of the two forces LAF and RAF, which are measured values, in order to release the loop section 39 formed in the flexible tube 35 and to change the flexible tube 35 into a substantially linear state. Such twisting information functions as supporting information for an operation of actually releasing the loop section 39 and changing the flexible tube 35 to the substantially linear state. That is, the providing device 150 provides the twisting direction necessary for releasing the loop section 39 and changing the flexible tube 35 to the substantially linear state as the twisting information. The twisting information includes at least one of a character 155a (see FIGS. 5A and 5C); a symbol 155b (see FIG. 5B); a numerical value of force 155c (see FIG. 5C); light emission (see FIGS. 5D and 5E); a sound 155h (FIGS. 1 and 5F); a fragrance; and vibration, which will be briefly described.

The providing device 150 may provide the twisting information to a monitor as a display. A position of the display is not particularly limited, as long as the operator can visually recognize the display. As a result, the twisting information may be displayed to be overlapped with an image 151 or an image 153, or may be displayed at a different position from the image 151 or the image 153.

As shown in FIG. 5A, the providing device 150 may display the twisting information as the character 155a such as "twist in the clockwise direction".

Figure 5B:
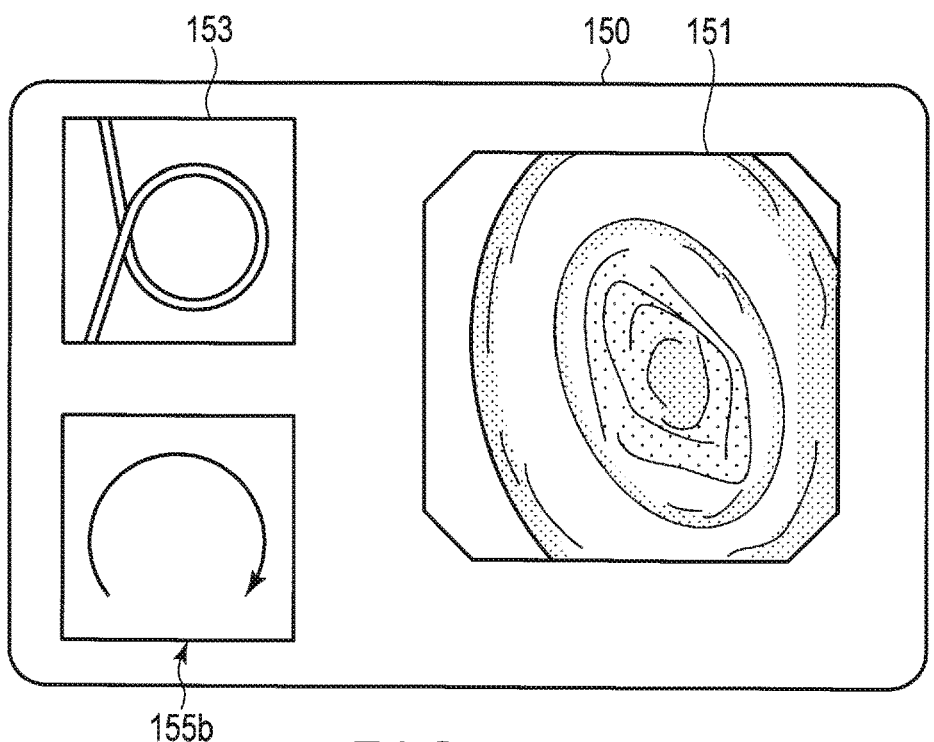
FIG. 5B is a diagram showing an example of providing twisting information.

As shown in FIG. 5B, the providing device 150 may display the twisting information as the symbols 155b. The symbols 155b include, for example, an arrow.

Figure 5C:
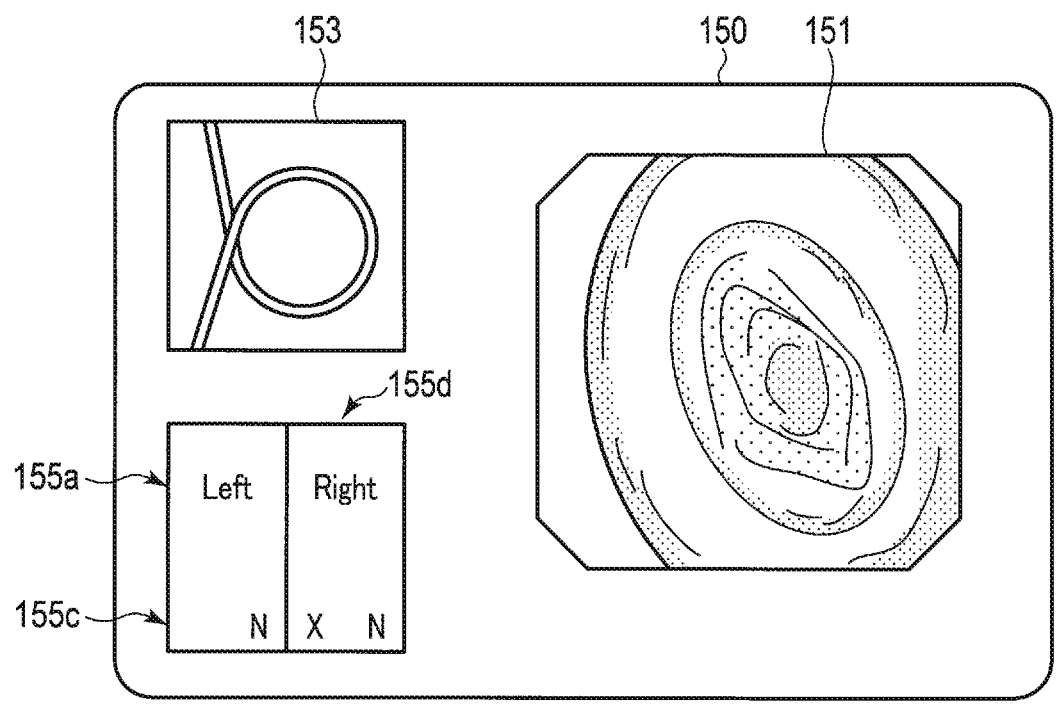
FIG. 5C is a diagram showing an example of providing twisting information.

As shown in FIG. 5C, the providing device 150 may display the twisting information as the character 155a indicating the twisting direction and the numerical value of force 155c (unit: N (newton)). The numerical value 155c indicates the twisting force of the operator required to change the flexible tube 35 to a substantially linear state by, for example, releasing the loop section 39, and applied from the one hand to the hand side of the flexible tube 35. The numerical value 155c may be calculated by the force calculator 61b based on the forces LAF and RAF, for example. FIG. 5C shows an example of a display area 155d for displaying the twisting information. In this case, it is necessary to twist to the right. A right area of the display area 155d displays "Right", which is the character 155a indicating the twisting direction, and displays XN, which is the numerical value 155c. In this case, a left area of the display area 155d displays "Left", which is the character 155a indicating the twisting direction, while the numerical value 155c indicates an empty field. In this case, the left area of the display area 155d may not be displayed.

Figure 5D:
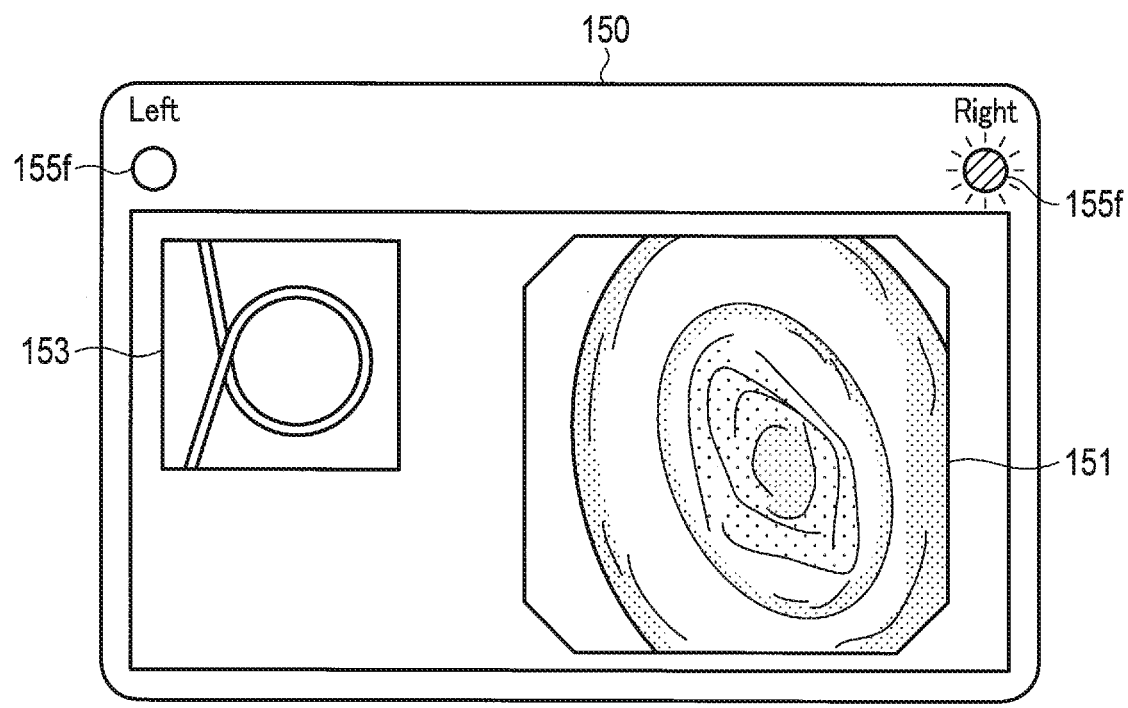
FIG. 5D is a diagram showing an example of providing twisting information.

As shown in FIGS. 5D and 5E, the providing device 150 may provide the twisting information as the light emission.

As shown in FIG. 5D, the providing device 150 may have light emitting sections 155f disposed on the monitor and configured to emit light. A position of each of the light emitting sections 155f is not particularly limited, as long as the operator can visually recognize the light emitting section 155f. A light emitting section 155f is disposed at a position different from the image 151 or the image 153, for example. A light emitting section 155f may be disposed so as to overlap the image 151 or the image 153. The image 151 or the image 153 on the monitor is a separate entity from the light emitting sections 155f, but may also serve as the light emitting sections 155f.

As shown in FIG. 5E, the providing device 150 may function as light emitting section 155gs that are disposed on the endoscope 20 and configured to emit light. For example, the light emitting sections 155g are disposed on the grip section 40. Each of the light emitting sections 155g disposed on the grip section 40 has, for example, an LED or the like. For example, the light emitting sections 155g may be disposed on the gripped portion 38 or an exposed portion of the flexible tube 35 disposed outside the pipeline section.

The light emitting sections 155f are provided for the left twist and the right twist, respectively. Only the light emitting section 155f in a direction necessary to twist is turned on or flickered according to the analysis result of the analyzer 85. The light emitting section 155f in a direction in which it is not necessary to twist is turned off. A single light emitting section 155f may be prepared and the single light emitting section 155f may emit light in a color corresponding to the twisting direction. The color corresponding to the twisting direction may be input and set in advance as desired by the input device 170, for example. While the description has been made using the light emitting sections 155f, such content is also applicable to the light emitting sections 155g.

As shown in FIGS. 1 and 5F, the providing device 150 may output the sound 155h corresponding to the twisting direction. The sound 155h corresponding to the twisting direction may be input and set in advance as desired by the input device 170, for example. The sound 155h includes, for example, a voice, a tone color, and the like. For example, the providing device 150 may be disposed inside the control device 80 or inside the grip section 40. The providing device 150 functions as a sound source or a speaker. For example, the providing device 150 may be disposed in a room in which the insertion apparatus 10 is disposed.

Although not shown, the providing device 150 may output the fragrance corresponding to the twisting direction. For example, the providing device 150 is disposed in the control device 80, the grip section 40, or the room in which the insertion apparatus 10 is disposed. Although not shown, the providing device 150 may output the vibration corresponding to the twisting direction. For example, the providing device 150 is disposed in the control device 80 or the grip section 40.

A method of operating the insertion apparatus 10 will be described with reference to FIG. 6.

When a push-operation of the flexible tube 35 is performed and the flexible tube 35 advances toward a deep part of a large intestine along an intestine wall of the large intestine, the state detector 50 detects the state information of the flexible tube 35 and the state calculator 81 calculates the shape information of the flexible tube 35 based on the state information. The shape information is displayed on the monitor of the providing device 150 as the bent shape of the flexible tube 35. The shape information is displayed on the monitor as the image 153.

The operator visually observes the monitor to determine whether or not the loop section 39 is formed in the flexible tube 35 (Step 1). In addition, the formation of the loop section 39 may be determined by the operator based on the sensation felt by the operator's hand gripping the hand side of the flexible tube 35 when the operator pushes the flexible tube 35 toward the deep part.

If the loop section 39 is not formed (Step 1: No), the push-operation of the flexible tube 35 is continuously performed, and the process returns to Step 1.

If the loop section 39 is formed (Step 1: Yes), the push-operation of the flexible tube 35 is interrupted. The hand side of the flexible tube 35 is twisted to the counterclockwise direction and the clockwise direction, respectively, around the central axis of the flexible tube 35 by one hand of the operator gripping the hand side of the flexible tube 35. As a result, the flexible tube 35 is twisted to the counterclockwise direction and the clockwise direction, respectively, around the central axis of the flexible tube 35 (Step 2). For example, the twisting may be each performed once. In such a twisting operation, for example, a left twisting operation in the counterclockwise direction is performed, and a right twisting operation in the clockwise direction is performed after the left twisting operation. The right twisting operation continues with the left twisting operation. The order of the left twisting operation and the right twisting operation is not particularly limited.

The external force detector 60 detects the external force LF in the counterclockwise direction and the external force RF in the clockwise direction, and calculates a force LAF of the external force LF and a force RAF of the external force RF. The external force detector 60 outputs the calculated forces LAF and RAF to the analyzer 85 (Step 3).

The analyzer 85 compares the force LAF and the force RAF with each other (Step 4).

In Steps 3 and 4, a comparison operation of the analyzer 85 is different according to Examples 1 to 5 of the arrangement positions of the external force detectors 60 shown in FIGS. 3A, 3B, 3C, 3D, and 3E.

The analyzer 85 determines whether or not the force RAF is smaller than the force LAF and outputs the determination result to the providing device 150 (Step 5).

Here, as an example, a calculation, a comparison, and a determination of the forces LAF and RAF corresponding to the shape and state of the loop section 39 in Steps 3 to 5 will be described using FIGS. 7A, 7B, 7C, 7D, and 7E, and Example 1 of the arrangement position of the external force detector 60. For the sake of clarity of illustration, the external force detector 60 is omitted in FIGS. 7A, 7B, 7C, 7D, and 7E.

For example, in Step 2, when the flexible tube 35 is twisted after the loop section 39 is formed in the flexible tube 35, the flexible tube 35 receives a reaction force from the intestine wall around the flexible tube 35 or the organs around the flexible tube 35. In addition, the reaction force is generated by contact between the flexible tubes 35 at the intersecting portion 39a. The loop section 39 indicates, for example, a clockwise direction portion of the flexible tube 35, a counterclockwise direction portion of the flexible tube 35, or an N-shaped portion of the flexible tube 35. The clockwise direction portion indicates a portion looping in the clockwise direction from the distal end of the flexible tube 35 toward the proximal end of the flexible tube 35. The counterclockwise direction portion indicates a portion looping in the counterclockwise direction from the distal end of the flexible tube 35 toward the proximal end of the flexible tube 35. The magnitude of a twisting force varies depending on the reaction force and the shape of the loop section 39. Therefore, the forces LAF and RAF vary.

Figure 7A:
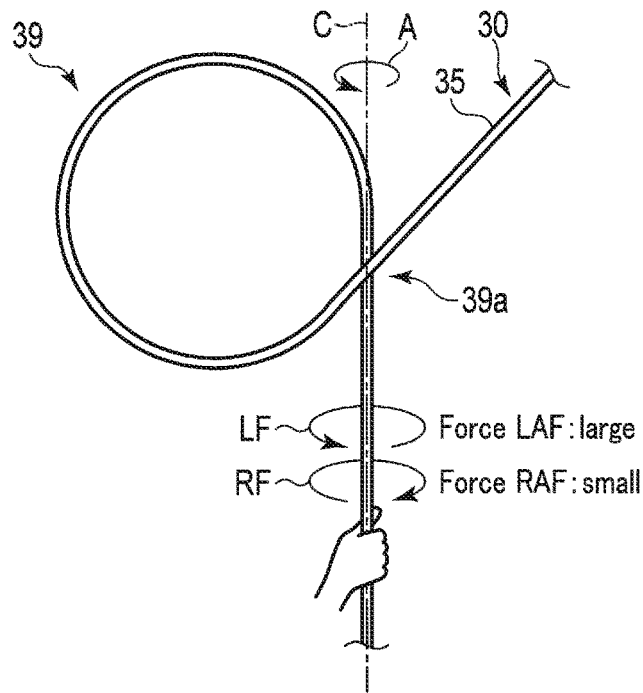
FIG. 7A is a diagram for explaining a calculation, a comparison, and a determination of forces LAF and RAF according to a shape and a state of a loop section.

As shown in FIG. 7A, for example, it is assumed that the loop section 39 is formed in the clockwise direction and the distal end section side of the flexible tube 35 is placed on the proximal end section side of the flexible tube 35 (hereinafter, referred to as pattern A).

In the pattern A, it is assumed that the twisting force (external force LF) in the counterclockwise direction is applied to the flexible tube 35. As a result, the entire loop section 39 and a plane on which the entire loop section 39 is disposed are rotated in the counterclockwise direction indicated by an arrow A around a central axis C of the flexible tube 35 including the intersecting portion 39a and the hand side. For this reason, the twisting force (external force LF) is increased and in Step 3, the external force detector 60 calculates a large force LAF.

In the pattern A, it is assumed that the twisting force (external force RF) in the clockwise direction is applied to the flexible tube 35. As a result, the loop section 39 intends to be eliminated. For this reason, the twisting force (external force RF) is reduced and in Step 3, the external force detector 60 calculates a small force RAF.

In addition, the analyzer 85 compares the large force LAF and the small force RAF with each other in Step 4, and determines that the force RAF is smaller than the force LAF in Step 5. Then, the flow of the operation method proceeds to Step 6.

Figure 7B:
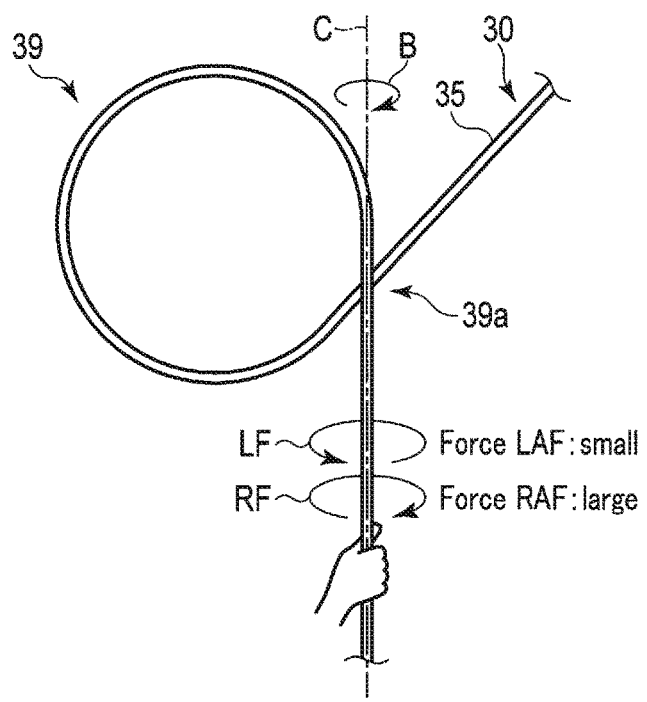
FIG. 7B is a diagram for explaining a calculation, a comparison, and a determination of the forces LAF and RAF according to a shape and a state of the loop section.

As shown in FIG. 7B, for example, it is assumed that the loop section 39 is formed in the clockwise direction and the proximal end section side of the flexible tube 35 is placed on the distal end section side of the flexible tube 35 (hereinafter, referred to as pattern B).

In the pattern B, it is assumed that the twisting force (external force LF) in the counterclockwise direction is applied to the flexible tube 35. As a result, the loop section 39 intends to be eliminated. For this reason, the twisting force (external force LF) is reduced and in Step 3, the external force detector 60 calculates a small force LAF.

In the pattern B, it is assumed that the twisting force (external force RF) in the clockwise direction is applied to the flexible tube 35. As a result, the entire loop section 39 and a plane on which the entire loop section 39 is disposed are rotated in the clockwise direction indicated by an arrow B around the central axis C of the flexible tube 35 including the intersecting portion 39a and the hand side. For this reason, the twisting force (external force RF) is increased and in Step 3, the external force detector 60 calculates a large force RAF.

In addition, the analyzer 85 compares the small force LAF and the large force RAF with each other in Step 4, and determines that the force RAF is larger than the force LAF in Step 5. Then, the flow of the operation method proceeds to Step 7.

Figure 7C:
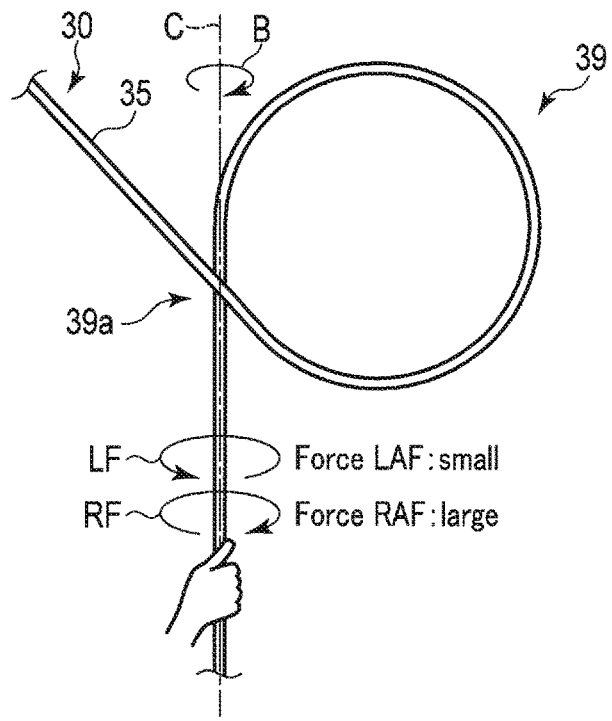
FIG. 7C is a diagram for explaining a calculation, a comparison, and a determination of the forces LAF and RAF according to a shape and a state of the loop section.

As shown in FIG. 7C, for example, it is assumed that the loop section 39 is formed in the counterclockwise direction and the distal end section side of the flexible tube 35 is placed on the proximal end section side of the flexible tube 35 (hereinafter, referred to as pattern C).

In the pattern C, it is assumed that the twisting force (external force LF) in the counterclockwise direction is applied to the flexible tube 35. As a result, the loop section 39 intends to be eliminated. For this reason, the twisting force (external force LF) is reduced and in Step 3, the external force detector 60 calculates a small force LAF.

In the pattern C, it is assumed that the twisting force (external force RF) in the clockwise direction is applied to the flexible tube 35. As a result, the entire loop section 39 and a plane on which the entire loop section 39 is disposed are rotated in the clockwise direction indicated by an arrow B around the central axis C of the flexible tube 35 including the intersecting portion 39a and the hand side. For this reason, the twisting force (external force RF) is increased and in Step 3, the external force detector 60 calculates a large force RAF.

In addition, the analyzer 85 compares the small force LAF and the large force RAF with each other in Step 4, and determines that the force RAF is larger than the force LAF in Step 5. Then, the flow of the operation method proceeds to Step 7.

Figure 7D:
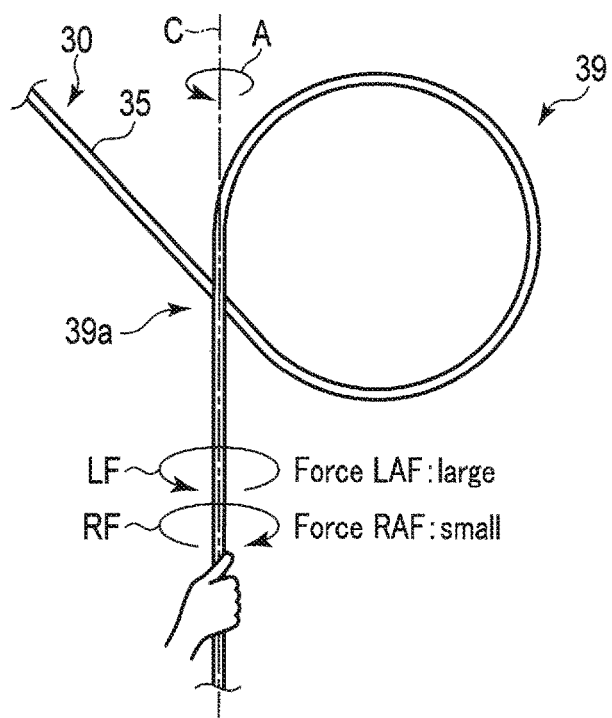
FIG. 7D is a diagram for explaining calculation, comparison, and determination of the forces LAF and RAF according to a shape and a state of the loop section.

As shown in FIG. 7D, for example, it is assumed that the loop section 39 is formed in the counterclockwise direction and the proximal end section side of the flexible tube 35 is placed on the distal end section side of the flexible tube 35 (hereinafter, referred to as pattern D).

In the pattern D, it is assumed that the twisting force (external force LF) in the counterclockwise direction is applied to the flexible tube 35. As a result, the entire loop section 39 and a plane on which the entire loop section 39 is disposed are rotated in the counterclockwise direction indicated by an arrow A around a central axis C of the flexible tube 35 including the intersecting portion 39a and the hand side. For this reason, the twisting force (external force LF) is increased and in Step 3, the external force detector 60 calculates a large force LAF.

In the pattern D, it is assumed that the twisting force (external force RF) in the clockwise direction is applied to the flexible tube 35. As a result, the loop section 39 intends to be eliminated. For this reason, the twisting force (external force RF) is reduced and in Step 3, the external force detector 60 calculates a small force RAF.

In addition, the analyzer 85 compares the small force LAF and the large force RAF with each other in Step 4, and determines that the force RAF is smaller than the force LAF in Step 5. Then, the flow of the operation method proceeds to Step 6.

As shown in FIG. 7E, for example, it is assumed that the loop section 39 is formed in an N shape (hereinafter, referred to as pattern E).

In the pattern E, it is assumed that the twisting force (external force RF) in the clockwise direction is applied to the flexible tube 35. As a result, the loop section 39 intends to be eliminated. For this reason, the twisting force (external force RF) is reduced and in Step 3, the external force detector 60 calculates a small force RAF.

In the pattern E, it is assumed that the twisting force (external force LF) in the counterclockwise direction is applied to the flexible tube 35. As a result, the entire loop section 39 and a plane on which the entire loop section 39 is disposed are rotated in the clockwise direction indicated by the arrow B around the central axis C of the flexible tube 35 including the hand side. For this reason, the twisting force (external force LF) is increased and in Step 3, the external force detector 60 calculates a large force LAF.

In addition, the analyzer 85 compares the small force RAF and the large force LAF with each other in Step 4, and determines that the force LAF is larger than the force RAF in Step 5. Then, the flow of the operation method proceeds to Step 7.

For example, if the force RAF is smaller than the force LAF (Step 5: Yes), the providing device 150 provides twisting information regarding a twisting direction of the small force RAF. In this case, the twisting information indicates, for example, that the flexible tube 35 is instructed to be twisted in the clockwise direction. Therefore, the providing device 150 provides an instruction to twist the flexible tube 35 in the clockwise direction (Step 6). After the instruction is provided, the operation ends.

For example, if the force RAF is larger than the force LAF (Step 5: No), the providing device 150 provides twisting information regarding a twisting direction of the small force LAF. In this case, the twisting information indicates, for example, that the flexible tube 35 is twisted in the counterclockwise direction. Therefore, the providing device 150 provides an instruction to twist the flexible tube 35 in the counterclockwise direction (Step 7). After the instruction is provided, the operation ends.

In general, a running state of the flexible tube 35 in the large intestine and a length of the large intestine are different for each patient. In addition, the insertion technique also differs by each operator who operates the flexible tube 35. The shape and size of the formed loop section 39 differ depending on these differences and the hardness and thickness of the flexible tube 35. When the operator performs the twisting operation on a hand side of the flexible tube 35 with one hand while the operator grips the hand side of the flexible tube 35 with one hand, the difference in the shape and size of the loop section 39 changes tactile information, which is transmitted from the hand side of the flexible tube 35 to one hand, and which is a different sense of resistance for each operator.

Therefore, in the present embodiment, the tactile information is calculated by the external force detector 60 as quantitative information such as the forces LAF and RAF of the external forces LF and RF applied to the flexible tube 35. In addition, in the present embodiment, the forces LAF and RAF are analyzed by the analyzer 85 and the twisting information is provided by the providing device 150 based on the analysis result. In addition, in the present embodiment, the twisting information is provided based on the forces LAF and RAF rather than providing the twisting information based on the shape information of the flexible tube 35. Therefore, in the present embodiment, the tactile information can be calculated as the quantitative information and the twisting information can be provided as support information for the insertion in which the loop section 39 is eliminated and the flexible tube 35 is changed to a substantially linear state based on the calculation result.

In the present embodiment, the twisting direction of the flexible tube 35 for releasing the loop section 39 and changing the flexible tube 35 to the substantially linear state is provided to the operator as the twisting information. Therefore, it is possible to provide a correct twisting direction to the operator, thereby improving safety of the insertion operation, reducing a pain of the patient, and improving an arrival rate of the flexible tube 35 to the deep part. In the present embodiment, even if the operator is an operator skilled in a twisting operation (hereinafter, referred to as an expert) or an operator with less experience in the twisting operation (hereinafter, referred to as an inexperienced person), accurate support information can be uniformly provided.

In the present embodiment, only one external force detector 60 is disposed, the external force detector 60 is disposed on the gripped portion 38 of the flexible tube 35 to be gripped or the periphery of the intersecting portion 39a of the loop section 39 formed in the flexible tube 35. Thus, the force at the gripped portion 38 or the periphery of the intersecting portion 39a can be reliably detected. In addition, the number of the external force detectors 60 can be minimized, and the constitution of the insertion apparatus 10 can be simplified.

In the present embodiment, for example, external force detectors 60 are disposed to be spaced apart from each other at substantially equidistant intervals. For example, the external force detectors 60 are disposed within a range from the distal end section of the flexible tube 35 to the gripped portion 38. Therefore, in the present embodiment, it is possible to dispense with changing the arrangement position of the external force detector 60 for each patient.

In the present embodiment, the external force detector 60 may also serve as the state detector 50 as the fiber sensor and the state calculator 81. Therefore, in the present embodiment, it is not necessary to introduce a large and complicated apparatus to calculate the shape information, and the shape information can be calculated with a simple and compact constitution. In addition, in the present embodiment, the presence or absence of the loop section 39 and the position of the external force detector 60 can be determined on the monitor, detection accuracy of the twisting direction can be improved, the twisting operation can be performed on the flexible tube 35 in a state in which the shape of the flexible tube 35 is observed through the monitor.

In the present embodiment, for example, it is assumed that the state detector 50 in the external force detector 60 is mounted as a magnetic coil. In this case, if a radio wave condition is not good, the shape information of the flexible tube 35 or the position of the flexible tube 35 may not be calculated accurately, and the shape information or position may not be accurately displayed on the monitor. However, the detection accuracy of the twisting direction can be improved by disposing the sensors 61a of the external force detector 60 in addition to the magnetic sensor of the state detector 50. In addition, if the radio wave condition is not good under a situation in which the magnetic coil is used, the shape information of the flexible tube 35 or the position of the flexible tube 35 may not be calculated accurately, and the shape information or position may not be accurately displayed on the monitor. However, when the state detector 50 is mounted as the fiber sensor, it is not necessary to consider the radio wave condition, and the shape information or the position can be accurately calculated, and the shape information or the position can be accurately displayed on the monitor and the support information can be provided.

In the present embodiment, the position of the probe 190 with respect to the flexible tube 35 in the direction of the central axis of the flexible tube 35 is adjusted by a movement of the probe 190. That is, the probe 190 is positioned relatively to the flexible tube 35. Therefore, the position of the external force detector 60 can be adjusted according to the patient or the situation, so that the external force can be detected with high accuracy.

In addition, the present invention is not limited to the above embodiments, and it is possible for the present application to be modified in various ways within the scope of the present invention without departing from the gist of the present application. In addition, the above embodiments may be implemented by appropriately combining them and in such a case, the combined effect is obtained. Furthermore, the above embodiment includes various steps of the invention, and various inventions can be extracted by an appropriate combination selected from constituent elements disclosed. For example, even if some of the constituent elements are deleted from all the constituent elements shown in the embodiments, if the problem can be solved and the effect can be obtained, the constitution in which the constituent elements are deleted can be extracted as the invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A flexible tube insertion apparatus comprising:
    a flexible tube having flexibility and configured to be inserted into an object;
    one or more external force detectors disposed on the flexible tube and configured to detect external forces applied to the flexible tube when the flexible tube is twisted in at least one direction; and
    a processor comprising hardware, the processor being configured to:
        compare an external force in a counterclockwise direction and an external force in a clockwise direction, which are detected by the one or more external force detectors, with each other when the flexible tube is twisted in the counterclockwise direction and the clockwise direction, respectively, around a central axis of the flexible tube, and output an analysis result; and
        provide twisting information regarding a twisting direction of the flexible tube for releasing a loop section formed in the flexible tube based on the comparison.

2. The flexible tube insertion apparatus according to claim 1, wherein
    when the one or more external force detectors comprise only one external force detector, the one external force detector is disposed at a position where the external force is applied to the flexible tube or a reaction force is generated by twisting, and
    when the one or more external force detectors comprise a plurality of external force detectors, the plurality of external force detectors are disposed within a range from a distal end section of the flexible tube to a gripped portion of the flexible tube.

3. The flexible tube insertion apparatus according to claim 1,
    wherein the one or more external force detectors comprise a plurality of external force detectors for detecting a plurality of external forces, and the processor is configured to:
    calculate an N-th force, where N is a natural number of one or more, from a maximum force in the plurality of external forces in a first direction around the central axis that are detected by the plurality of external force detectors and compare the N-th force with the external force in a direction opposite to the first direction at an arrangement position of a corresponding external force detector that has calculated the N-th force,
    analyze a portion of the flexible tube in which a change in the external force is a maximum before and after twisting from the external forces in the first direction and compare the external force in the counterclockwise direction and the external force in the clockwise direction at the portion where the change in the external force is the maximum with each other, and one of:
        compare the external force in the counterclockwise direction and the external force in the clockwise direction that are detected by the one or more external force detectors disposed at a position where a reaction force is generated by the twisting with each other, or
        compare a total sum of the external forces in the counterclockwise direction calculated by each of the plurality of external force detectors disposed within a range and a total sum of the external forces in the clockwise direction calculated by each of the plurality of external force detectors disposed within the range with each other.

4. The flexible tube insertion apparatus according to claim 1, wherein
    the one or more external force detectors comprise a sensor disposed on a peripheral surface of the flexible tube and configured to detect the external force; and the processor is configured to calculate the force based on the external force.

5. The flexible tube insertion apparatus according to claim 1, further comprising a probe configured to be inserted into the flexible tube,
   wherein the one or more external force detectors comprise a sensor disposed on a peripheral surface of the probe and configured to detect the external force; and
   the processor is configured to calculate the force based on the external force.

6. The flexible tube insertion apparatus according to claim 1, further comprising a state detector configured to detect state information of the flexible tube regarding a state of the flexible tube;
   wherein the processor is configured to calculate shape information of the flexible tube regarding a shape of the flexible tube along a direction of the central axis of the flexible tube based on the state information detected by the state detector,
   the shape information of the flexible tube includes position information of the one or more external force detectors, and
   the providing device displays the shape information.

7. The flexible tube insertion apparatus according to claim 6, wherein the one or more external force detectors serve as the state detector and the state calculator.

8. The flexible tube insertion apparatus according to claim 1,
   wherein the processor compares the force of the external force in the counterclockwise direction and the force of the external force in the clockwise direction with each other to determine a small force, and
   the providing device provides the twisting direction corresponding to the small force as the twisting information.

9. A flexible tube insertion apparatus comprising:
   a flexible tube having flexibility and configured to be inserted into an object;
   one or more external force detectors disposed on the flexible tube and configured to detect external forces applied to the flexible tube when the flexible tube is twisted in at least one direction; and
   a processor comprising hardware, the processor being configured to:
      provide twisting information regarding a twisting direction of the flexible tube for releasing a loop section formed in the flexible tube, according to a direction in which the flexible tube is twisted and the detected external forces; and
      calculate two external forces, which are measured values, wherein the twisting information includes information instructing the twisting direction of the flexible tube based on a result of a comparison of the two external forces, which are the measured values, in order to eliminate the loop section formed in the flexible tube and to change the flexible tube into a linear state.

10. The flexible tube insertion apparatus according to claim 9, wherein the twisting information includes at least one of a character, a symbol, a numerical value of the force, light emission, a sound and vibration.

* * * * *